United States Patent [19]
Lund et al.

[11] Patent Number: 5,582,577
[45] Date of Patent: Dec. 10, 1996

[54] SURGICAL RETRACTOR INCLUDING CENTRAL ELASTIC MEMBER

[75] Inventors: Greg O. Lund, Wasilla, Ak.; Frederick D. Roemer, Bloomington, Ind.

[73] Assignee: Vance Products Incorporated, Spencer, Ind.

[21] Appl. No.: 387,172

[22] Filed: Feb. 13, 1995

[51] Int. Cl.$^6$ ...................................................... A61B 17/00
[52] U.S. Cl. ........................... 600/204; 600/206; 600/208; 600/215; 600/233
[58] Field of Search ...................................... 600/201, 204, 600/206, 208, 209, 210, 215, 214, 217, 229, 233, 235, 236; 606/107, 191, 197, 199; 604/104, 105, 106

[56] References Cited

U.S. PATENT DOCUMENTS

| | | | |
|---|---|---|---|
| 497,064 | 5/1893 | Van Meter | 600/233 X |
| 1,947,649 | 2/1934 | Kadavy | 600/206 X |
| 2,701,562 | 2/1955 | Michael et al. | 600/206 X |
| 3,991,426 | 11/1976 | Flom et al. | 600/107 X |
| 4,274,398 | 6/1981 | Scott, Jr. | |
| 4,430,991 | 2/1984 | Darnell | |
| 5,085,664 | 2/1992 | Bozzo | 600/191 |
| 5,307,790 | 5/1994 | Byrne | 600/215 X |
| 5,374,272 | 12/1994 | Arpa et al. | 600/236 X |

FOREIGN PATENT DOCUMENTS 8000034   8/1981   Netherlands ............. 600/206

OTHER PUBLICATIONS

Miltex Instrument Co., Inc., *Miltex Surgical Instruments*, Lake Sucess, New York, 1986, p. 89.

*Primary Examiner*—Richard J. Apley
*Assistant Examiner*—Beverly M. Flanagan
*Attorney, Agent, or Firm*—Richard J. Godlewski

[57] ABSTRACT

A surgical retractor, retainer, tensioner, tenaculum, spreader or stabilizer (10) useful in open surgical procedures, or in laparoscopic or other endoscopic procedures, includes a plurality of tissue-engaging elements (12, 14) (such as a plurality of atraumatic hooks (18)) connected by a central elastic member (16). The elastic member (16) is preferably composed of a medical grade rubber, silicone or fluoropolymer elastomer, and is preferably configured or shaped as an O-ring (22) or regular polygon (66, 74, 88, or 92). When the retractor (10) is intended and particularly adapted for use in laparoscopic or other endoscopic procedures, the elastic member (16) is collapsible in a direction transverse to an imaginary line drawn between the plurality of tissue engaging elements (12, 14), so as to allow the retractor (10) to be passed through a surgical cannula into and out of the patient's body during the procedure. Alternatively, when the retractor (10) is intended and particularly adapted for use in any surgical procedure (that is, not limited to use in laparoscopic procedures), the elastic member (16) is directly connected to the plurality of tissue-engaging elements (12, 14), such that there are no disparate, rigid intermediate portions between the individual tissue-engaging elements (12, 14). The former embodiment is particularly advantageous in that retraction can be entirely performed within the body space enclosing the surgical site. Both embodiments are particularly advantageous in being of simple and inexpensive construction, yet allowing the elimination of the surgical assistant previously required for performing retraction, and saving the time needed for the surgeon to instruct such an assistant during retraction.

22 Claims, 8 Drawing Sheets

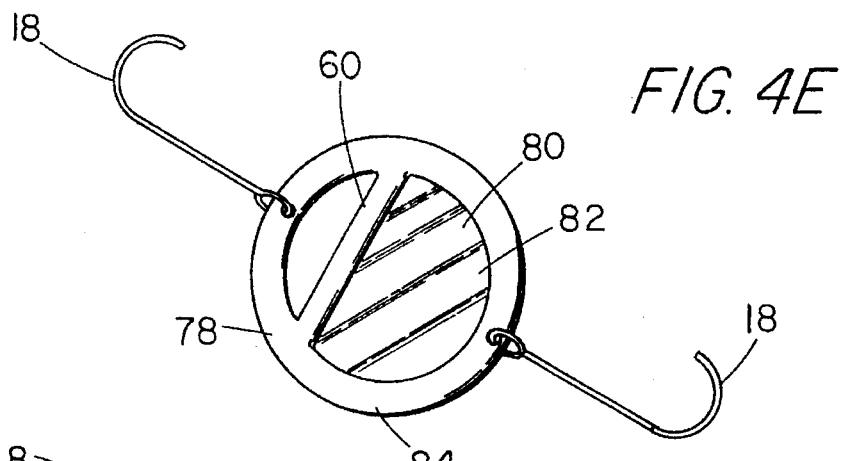
FIG. 4E
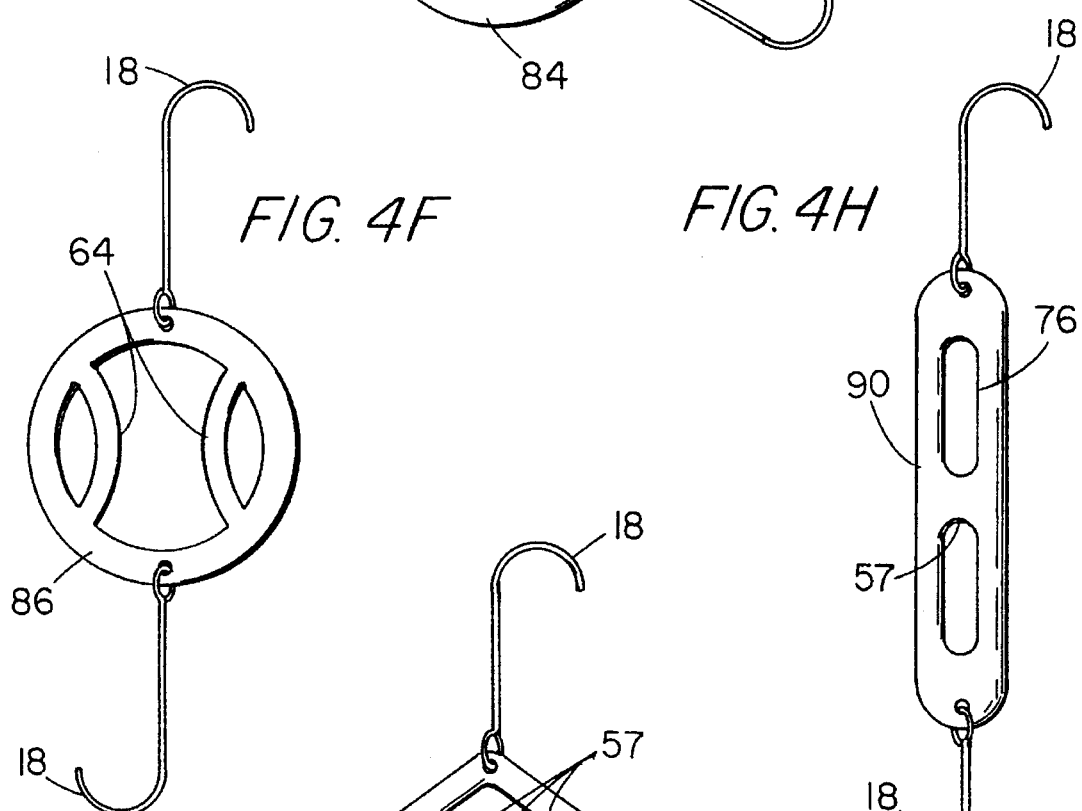
FIG. 4F
FIG. 4H
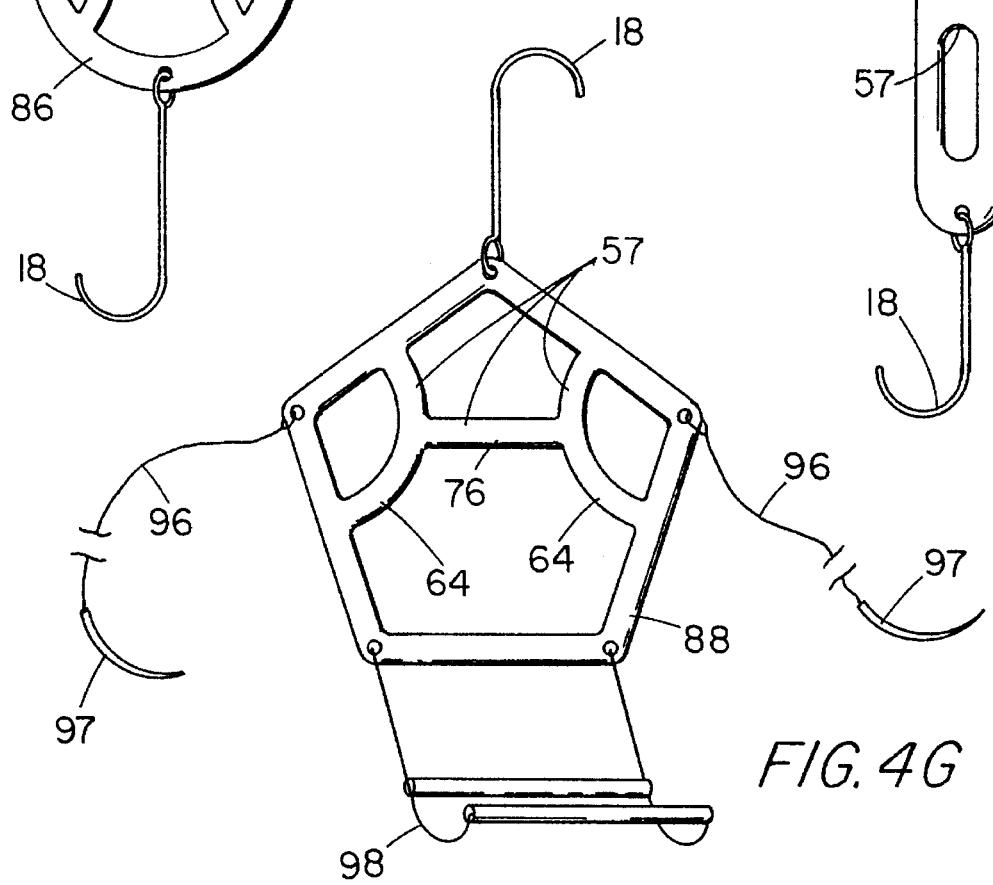
FIG. 4G

SURGICAL RETRACTOR INCLUDING CENTRAL ELASTIC MEMBER

TECHNICAL FIELD

This invention relates generally to surgical devices, and more particularly to surgical retractors, espcially retractors useful in laparoscopic procedures.

BACKGROUND OF THE INVENTION

The practice of percutaneous surgery has long been aided by the use of retractors, retainers, tensioners, tenacula, spreaders and stabilizers. While the details of their constructions vary, all hold various tissues together or apart, these tissues neighboring the surgical wound, and ease the surgeon's access to the specific tissues of interest at the surgical site. Significant drawbacks in the use of conventional retractors and the like include the need for one or more surgical assistants to operate the devices, and the considerable time needed for the surgeon to direct the assistants in the precise positioning of the devices; other problems exist as well.

Some but not all of these problems are addressed by the type of retractor disclosed in U.S. Pat. No. 4,274,398 (Scott, Jr., Jun. 23, 1981) and U.S. Pat. No. 4,430,991 (Darnell, Feb. 14, 1984). That type of device includes a rigid stainless steel frame which is conformed to fit the surface contour of the portion of the patient's body to be operated on, fully surrounding the surgical site. The device also includes at least one stay, the stay having an elastic member and tissue holding means, for example, a hook. The frame has a plurality of notches in which the elastic member of the stay is frictionally held, to retract tissue held by the tissue holding means. The device is asserted to be advantageous in eliminating the need for one or more surgical assistants who would otherwise be needed to retract the tissues.

While useful for its intended purpose, the key to the utility of that type of device—its large, rigid frame—prevents its use in laparoscopic and other endoscopic surgical procedures. Further, the drawbacks of the other conventional retractors mentioned above become even more acute in laparoscopic surgery. Laparoscopic surgical procedures are performed at a surgical site within an enclosed body space. In order to reduce pain to the patient, to speed the surgery itself and to speed the patient's recovery, access to the enclosed space is available through only a limited number of cannulae puncturing the skin and tissue overlying the surgical site. Because access to the space is intentionally limited, adequate retraction or engagement of tissues neighboring the surgical site can be problematic.

Despite these problems, retractors are still necessary and useful in laparoscopic and other endoscopic procedures. One type of retractor is elongated and includes a proximal handle portion (positioned outside the patient's body during use) and a distal tissue-engaging portion (positioned inside the body space during use). The tissue-engaging portion can be shaped, for example, as an atraumatic hook, a spreading fan or a relatively broad, curved blade. Another type of device is simply a pair of blunt tipped subcutaneous forceps, long enough to grasp and manipulate the tissues in the body space.

Several problems have been encountered in the use of such retractors, however. They necessarily extend through the patient's skin and tissues to the surgical site, and therefore require a puncture site and access port for their own individual and exclusive use. Their use thus causes additional discomfort to the patient for each retractor used. Moreover, the prior laparoscopic retractors often extend across the surgical site, interfering with the surgeon's ability to see the site and its neighboring tissues. Obstruction of the surgeon's view compounds the problems inherent in performing a surgical procedure in a closed space. While retraction of tissues neighboring the surgical site has also been performed by the use of long sutures (passed through the skin and tissues overlying the site, around the tissue to be engaged, and back through the overlying tissues and skin), such a procedure is time consuming and increases patient discomfort, and is generally not an adequate solution to the problems of retraction.

SUMMARY OF THE INVENTION

The foregoing problems are solved and a technical advance is achieved in an illustrative surgical retractor, retainer, tensioner, tenaculum, spreader or stabilizer. More particularly, in a first aspect the retractor or the like is particularly adapted for facile introduction into and removal from the body through a cannula during a laparoscopic or other endoscopic procedure, and comprises a plurality of tissue-engaging elements, and a central elastic member connecting the plurality of tissue-engaging elements, wherein the elastic member is collapsible in a direction transverse to an imaginary line drawn between the plurality of tissue-engaging elements, allowing the retractor to be passed through the cannula into and out of the body during the procedure.

Preferably, the elastic member comprises an O-ring or regular polygon composed of a medical grade rubber, silicone or fluoropolymer elastomer. Also preferably, the tissue-engaging elements are generally rigid, that is, more rigid or less elastic than the elastic member, so that it is the elastic member (rather than the tissue-engaging elements) which provides resiliency to the retraction achieved. Desirably, at least one (and preferably more) of the plurality of tissue-engaging elements comprises an atraumatic hook, although blade-type tissue-holding elements are also contemplated as advantageous within the invention. Also desirably, at least one (and preferably more) of the plurality of tissue-engaging elements is slidable along the elastic member during use, to ensure uniformity of the retraction provided.

The elastic member can include an interior brace, preferably elastic and formed continuously with the remainder of the elastic member. The elastic member can further or alternatively include an interior limiting web, such as a flexible but generally more inelastic membrane or mesh. The brace and web serve to more precisely define the elasticity of the elastic member, and allow different degrees of elasticity in different directions, if more than two tissue-engaging elements are employed.

In a second aspect of the present invention, the retractor or the like is not limited to use in laparoscopic or other endoscopic procedures, but is also useful in percutaneous procedures, and comprises a plurality of tissue-engaging elements, and a central elastic member directly connecting the plurality of tissue-engaging elements to one another. ("Directly" means that the retractor contains no disparate, rigid intermediate portions between the tissue-engaging elements.) In this second aspect, the retractor preferably and/or desirably comprises the various elements listed above with respect to the first aspect of the invention.

A third aspect of the invention is directed to a more specific laparoscopic retractor or the like, comparable to the first aspect of the invention, in which the elastic member comprises an O-ring of medical grade silicone elastomer, and in which the plurality of tissue-engaging elements are atraumatic hooks which are slidable along the O-ring.

A fourth aspect of the invention is similarly directed to a more specific laparoscopic retractor or the like, comparable to the third aspect but consisting of the elements of the third aspect. In this regard, it should be carefully noted that the present invention resides both in combinations comprising and in combinations consisting of the enumerated parts.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIGS. 4A through 4I are top views of other preferred embodiments of the present invention, the specific embodiments varying in the shape of the elastic member and in the number and type of the tissue-engaging elements;

DETAILED DESCRIPTION

Figure 1:
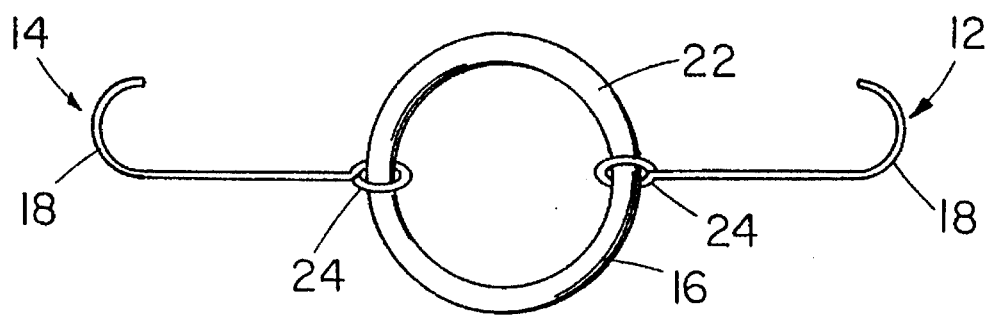
FIG. 1 is a perspective view of the preferred embodiment of the present invention.

With reference to FIG. 1, a first preferred embodiment of the surgical retractor, retainer, tensioner, tenaculum, spreader or stabilizer 10 according to the present invention is thereshown and first comprises a plurality of, and preferably a pair of, tissue-engaging elements 12 and 14. The retractor 10 also comprises a central elastic member 16 connecting the plurality of tissue-engaging elements, such as the elements 12 and 14, to one another. The tissue-engaging elements 12 and 14 each include an atraumatic hook 18 on one end. The elastic member 16 preferably comprises an O-ring 22, while the tissue-engaging elements 12 and 14 each further include a shank end 24 opposite the atraumatic hook 18. The shank ends 24 of the elements 12 and 14 are looped about the O-ring 22 without compressing it, thereby allowing the tissue-engaging elements 12 and 14 to slide along the elastic member 16, that is, along the O-ring 22.

The O-ring 22 or other elastic member 16 is composed of a medical grade elastomer, such as a rubber, a silicone or a fluoropolymer. The O-ring 22 or other elastic member 16 is thus collapsible to allow the retractor 10 to be passed through a cannula 100 (described in more detail below, with reference to FIGS. 6A through 6C). More particularly, the elastic member 16 is collapsible in at least a direction transverse to an imaginary line drawn between the tissue-engaging elements 12 and 14, that is, an imaginary line connecting them. Preferably, the elastic member 16 directly connects the tissue-engaging elements 12 and 14, that is, the retractor 10 contains no disparate, rigid intermediate portions between the elements 12 and 14.

Figure 2A:
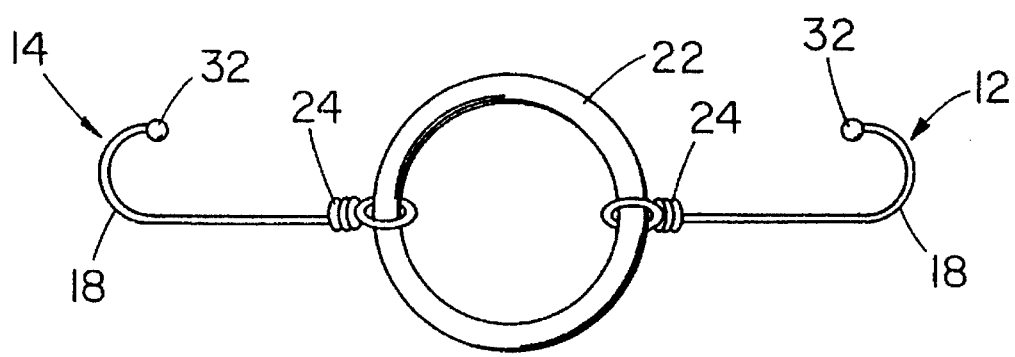
FIGS. 2A through 2C are top views of other preferred embodiments of the present invention.
Figure 2B:
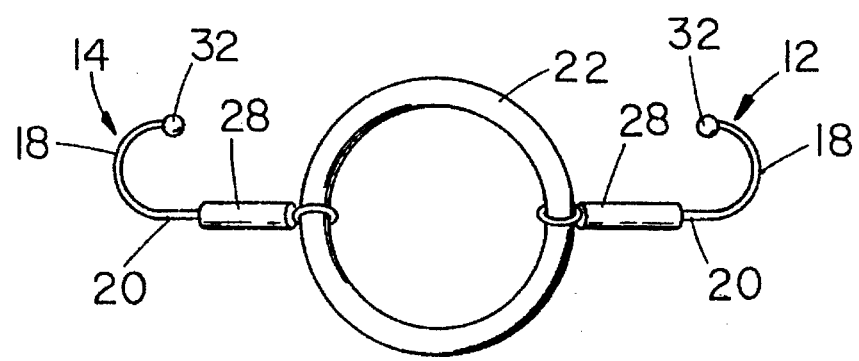
Figure 2C:
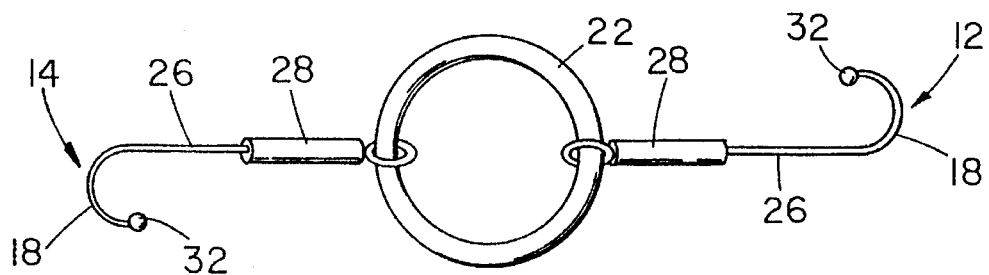

While the shank ends 24 of the tissue-engaging elements 12 and 14 can merely be looped once about the elastic member 16, as shown in FIG. 2A the shank end 24 of each element 12 and 14 can further be twisted or wrapped about itself, to more securely attach the elements 12 and 14 to the elastic member 16, while simultaneously ensuring that the shank ends 24 do not collapse on the member 16, and prevent the elements 12 and 14 from sliding along the member 16. As shown in FIGS. 2B and 2C, the shank ends 24 of the tissue-engaging elements 12 and 14 can also be covered with sleeves 28, composed of stainless steel or medical grade plastic.

FIGS. 2A through 2C further show that the atraumatic tissue-engaging elements 12 and 14 can be configured in a variety of ways. For example, one or both of the elements 12 and 14 can be relatively shorter (as shown by hook shanks 20) or relatively longer (as shown by hook shanks 26). The hooks 18 can include ball welds 32 on their points, so as to ensure that the hooks 18 do not traumatize the tissue with which they are engaged. Should it be desired that the position of the tissue-engaging elements 12 and 14 be fixed relative to O-ring 22, shank ends 24 can be tightly wrapped to fixedly engage O-ring 22.

Figure 3:
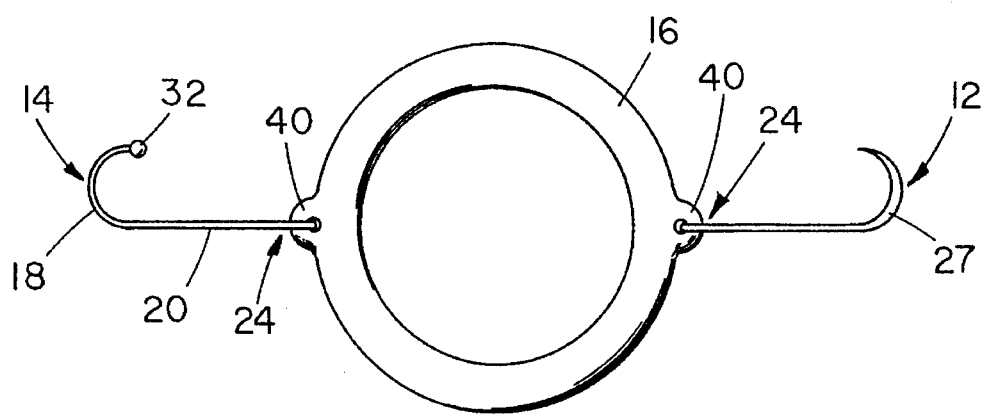
FIG. 3 is a top view of another preferred embodiment of the present invention.

FIG. 3 discloses an alternative preferred embodiment of the present invention in which the tissue-engaging elements 12 and 14 are not free to slide along the elastic member 16. Instead, the elastic member 16 includes a pair of perforate lobes 40 through which the shank ends 24 of the elements 12 and 14 pass. This fixed position may be desirable, depending upon the surgery being performed.

As another alternative, the tissue-engaging elements 12 and 14 need not be configured solely as hooks. One, both or all of the plurality of tissue-engaging elements (for example, the element 12) can be shaped like a conventional blade-type tissue-engaging element 27.

Figure 5A:
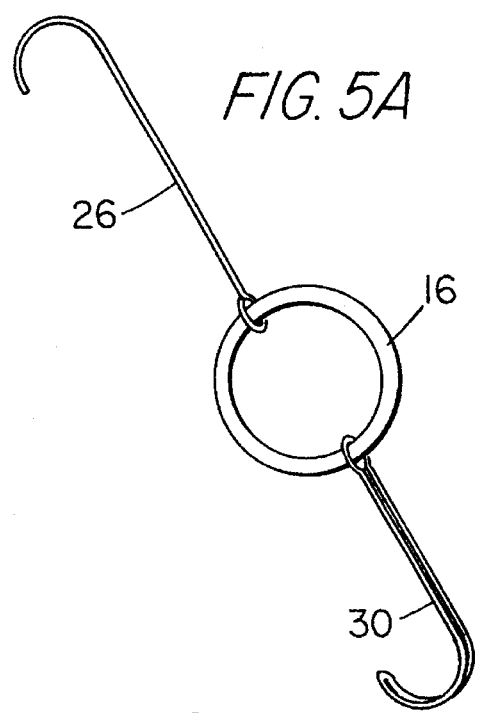
FIGS. 5A through 5H are top or perspective views of other preferred embodiments of the present invention, the specific embodiments varying in the number and type of tissue-engaging elements.
Figure 5C:
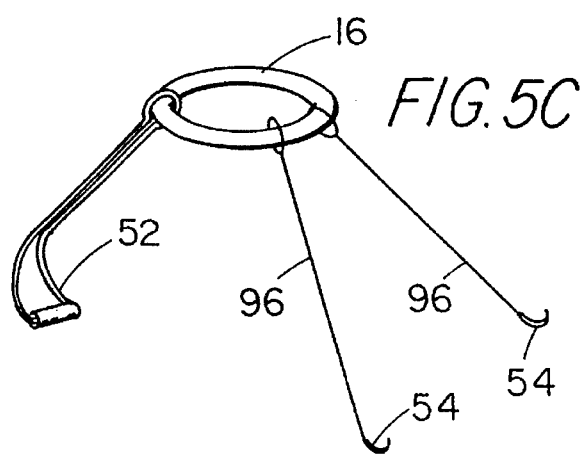
Figure 5B:
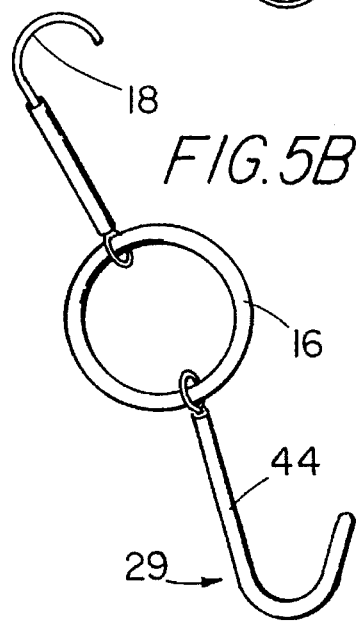
Figure 5D:
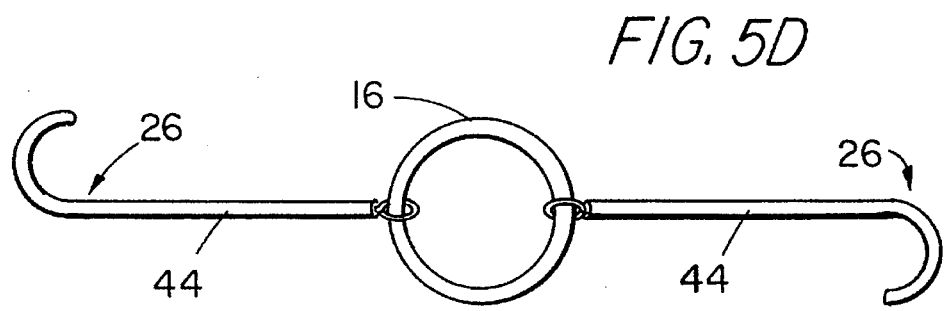
Figure 5E:
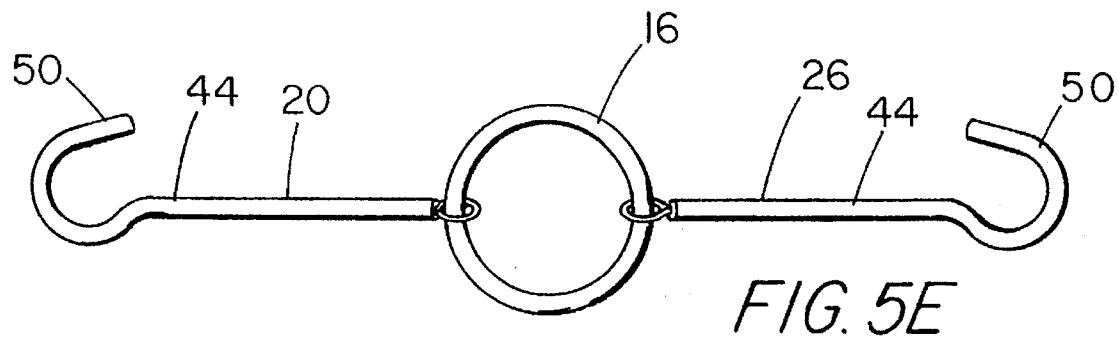
Figure 5F:
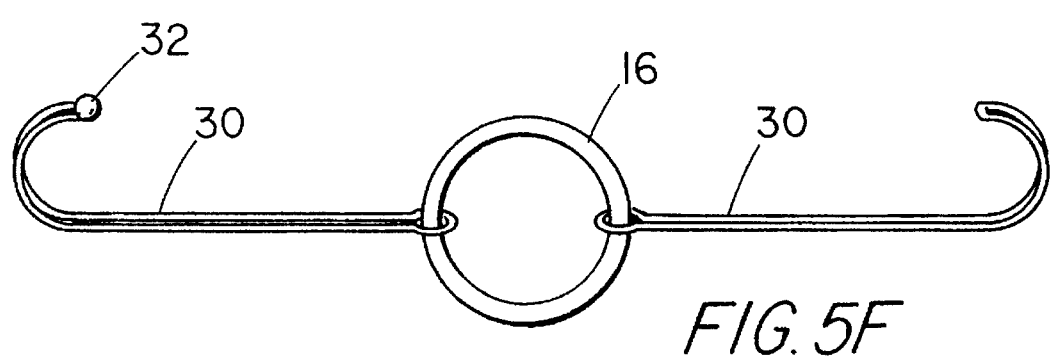
Figure 5G:
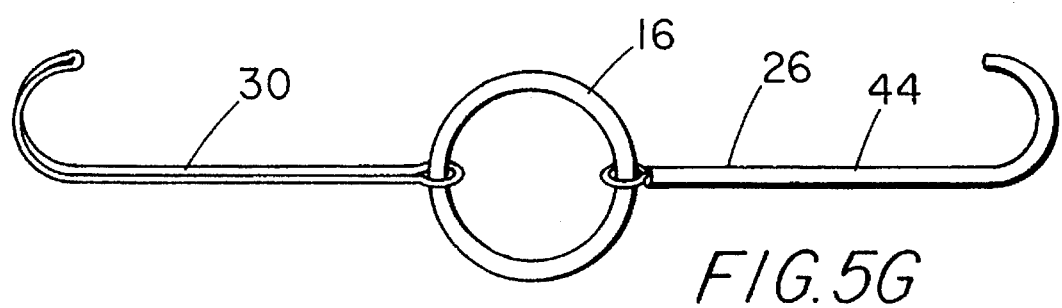
Figure 5H:
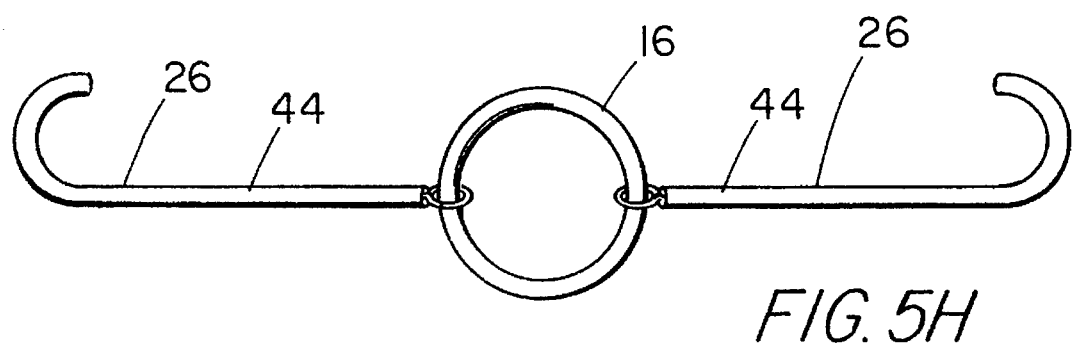

Of course, when configured as hooks, the tissue-engaging elements 12 and 14 can take any of a variety of shapes, depending upon the particular use to which the retractor 10 will be put. Such a variety of hook configurations is shown in FIGS. 5A through 5H. For example, FIGS. 5A, 5F and 5G each disclose tissue-engaging elements configured as a double wire hook 30. FIGS. 5B, 5D, 5E, 5G and 5H each disclose hooks and/or hook shanks covered with a coating 44 of medical grade plastic, silicone or the like. FIG. 5B in particular shows a tissue-engaging element shaped as a hook 29 which is slightly open, that is, which turns on itself less than 180 degrees. FIG. 5E further shows a tissue-engaging element shaped as a hook 50 which is reflex-curved, like a shepherd's staff. Of course, as should be evident from the Figures, the variety of hooks serving as the tissue-engaging elements can point in either direction, as is convenient for their intended use.

The retractor 10 of the present invention enjoys a wide range of utility. For example, depending upon the specific tissues present at the particular surgical site, the preferred or optimal tissue-engaging elements may not be hooks at all. A retractor having such a configuration is shown in FIG. 5C, in which one tissue-engaging element is shaped as a stirrup 52, while other tissue-engaging elements are formed as relatively inelastic (that is, less elastic than the elastic member 16) suture threads or tethers 96 bearing on them small suture needles 54. In use, the suture needles 54 are used to suture one side of the elastic member 16 to the appropriate tissue, for example, a more rigid body structure, while the stirrup 52 engages other, less rigid body tissue.

Figure 4A:
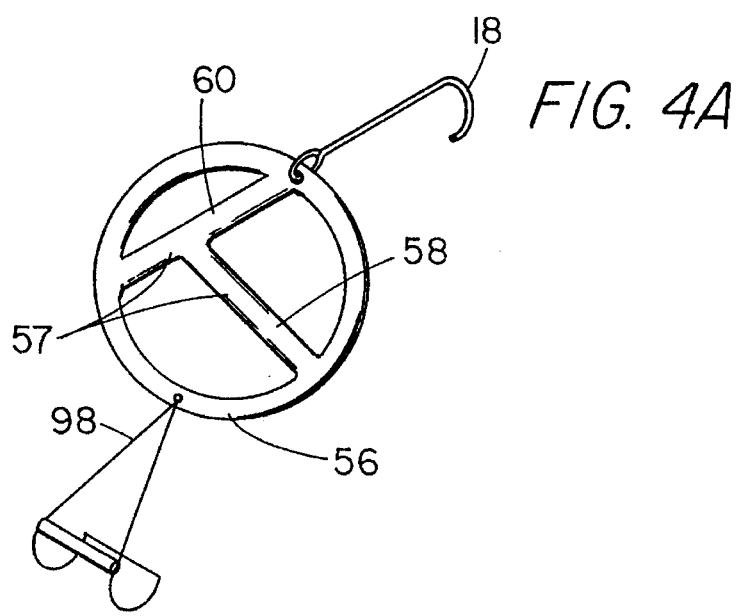
Figure 4B:
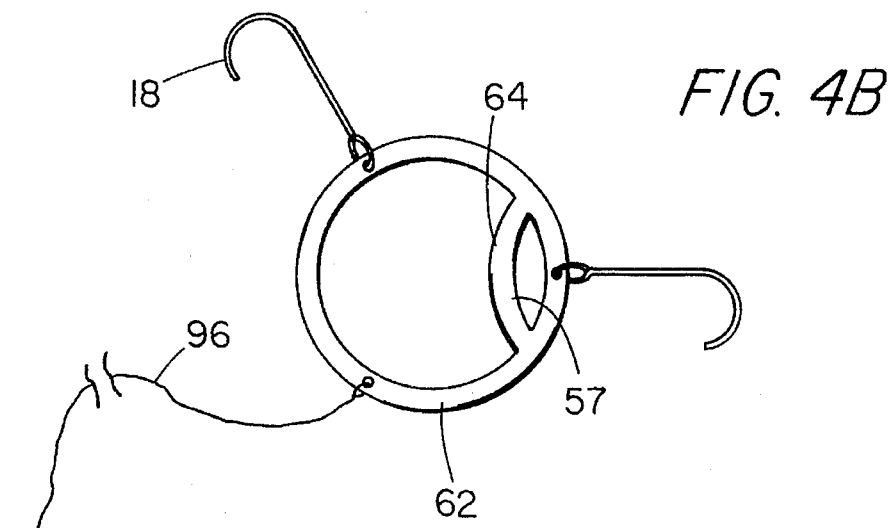

Of course, adaptation of the retractor 10 to particular uses may entail modification of the shape of the elastic member 16 from the simple O-ring 22 of FIG. 1. Modifying the shape of the elastic member allows control of the precise elasticity of the member, especially in different directions when more than two tissue-engaging elements are employed. A number of modifications to the elastic member 16 are shown in FIGS. 4A through 4I. For example, FIG. 4A shows a retractor including an elastic member 56 which is shaped as a circle which includes a pair of braces or bolsters 57 formed as two internal chords 58 and 60. FIG. 4B discloses a retractor which includes an elastic member 62 similar to the elastic member 56 of FIG. 4A, but which has a single brace 57 formed as an arc 64. FIG. 4F shows a retractor having a circular elastic member 86 like the member 62, but with a pair of bracing arcs 64.

Figure 4C:
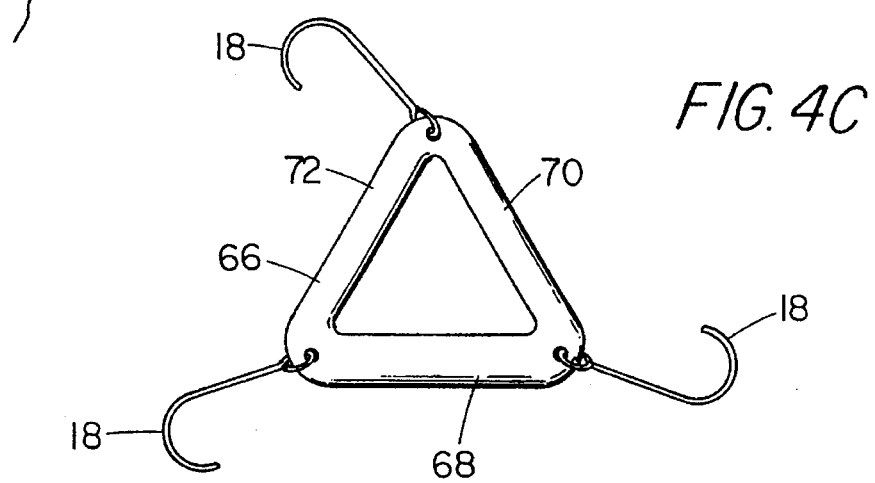
Figure 4D:
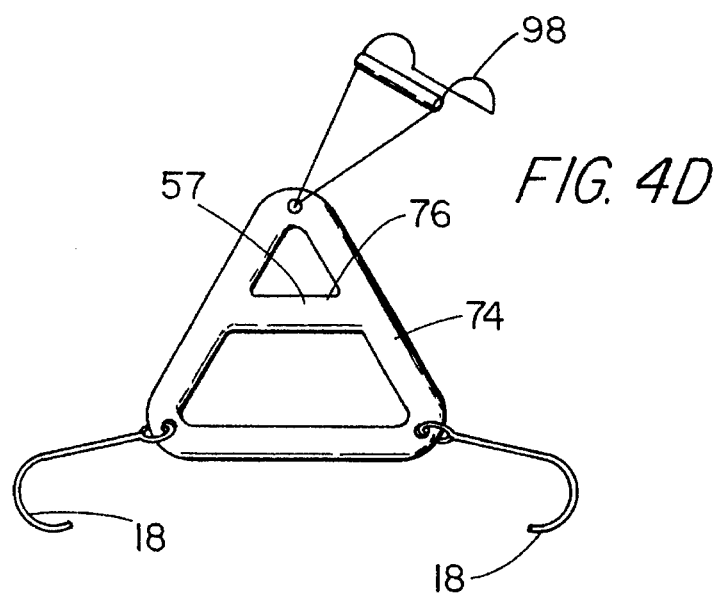

The elastic member 16 need not be circular, and instead can be shaped as a regular polygon or other form. FIG. 4C shows a retractor having an elastic member shaped as a triangle 66 having one side 68 which is thicker than the other sides 70 and 72. This allows the hooks 18 to experience different levels of retractive tension during use. FIG. 4D shows a retractor including a triangular elastic member 74 similar to the triangle 66 but having a brace 57 formed as a straight portion 76. FIG. 4G discloses a retractor with an elastic member shaped as a pentagon 88, with a plurality of braces 57 formed as one straight portion 76 and a pair of arcs 64. Alternatively, as shown in FIG. 4H, the elastic member can simply be an elongated body 90, with an internal brace 57 formed as a straight portion transversely across longitudinal members 76 of the elongated body 90.

Figure 4I:
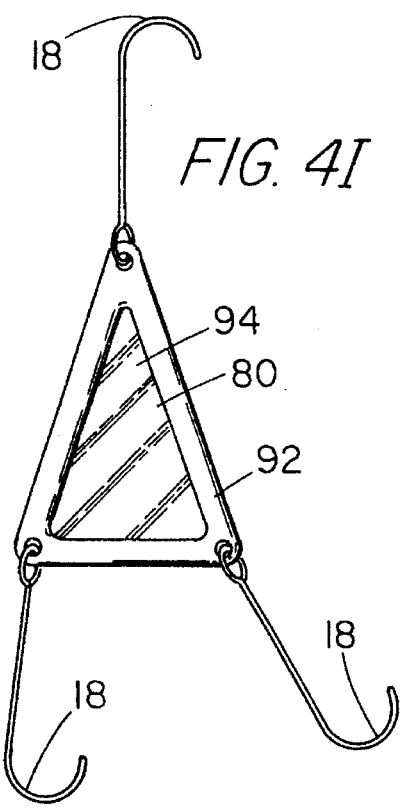

The elasticity of the elastic member 16 of the retractor 10 can be controlled in other ways. For example, FIG. 4E discloses a retractor with a circular elastic member 78 similar to the member 56 of FIG. 4A, and which similarly includes an internal chord 60, but which also includes a limiting web 80 formed as a continuous, flexible membrane 82. The membrane 82 extends between the chord 60 and an opposing part of the periphery 84 of the circular elastic member 78. FIG. 4I discloses a retractor whose elastic member is configured as an elongated triangular body 92 having a limiting web 80 formed as an interior, inelastic but flexible mesh 94.

The embodiments shown in FIGS. 4A through 4I include a variety of tissue-engaging members, many of which have been discussed in relation to other embodiments, and their characteristics need not be repeated. Of interest are the wrap-type tissue-engaging elements 98 of FIGS. 4A, 4D and 4G, which are attached to their respective elastic members 56, 74 and 88 by relatively inelastic bent wires. The elements 98 permit a tubular tissue (such as a blood vessel or the like) to be safely retracted without danger of puncture or breach. Also of interest are the large suture needles 97 of the retractor shown in FIG. 4G, attached to elastic member 88 by suture threads or tethers 96. In contrast to the elements 98, however, engagement of the suture threads 96 of the elastic member 88 with the appropriate tissue is achieved by puncturing, piercing or breaching the tissue with the needles 97. The needles 97 serve the same purpose as the suture needles 54 shown in FIG. 5C and discussed above. As depicted in FIG. 4B, one of the tissue-engaging members is suture thread or tether 96, which can be secured to tissue within the minimally invasive surgical field. Alternatively, the length of this suture thread or tether 96 can be increased to be percutaneously drawn outside the surgical field or simply drawn through an introducer sheath and manipulated or secured by the surgeon. The suture tether can be fixedly secured to elastic member 62 or looped around the member to slide freely therealong.

It is abundantly clear that the retractor of the present invention permits a wide range of adaptations to a wide range of specific surgical conditions of use. Despite such high versatility, however, the use of any of the preferred embodiments of the present invention as described is very straightforward. For sake of simplicity, reference will be had to the embodiment shown in FIG. 1. With additional reference to FIGS. 6A through 6C, a simplified schematic view of a laparoscopic or other endoscopic surgical procedure performed with the retractor 10 of the present invention is shown, in which communication of three cannulae 100, 102 and 104 with an enclosed body space 106 has already been established. By way of example, in a laparoscopic dissection of pelvic lymph nodes (not shown), the body space 106 is located adjacent the obturator fossa (also not shown). Communication of the cannulae 100, 102 and 104 with the body space 106 can be established by any of a variety of standard medical procedures already familiar to those skilled in the art, which for the sake of brevity are omitted here. Also, for clarity, the laparoscopic viewing cannula has been omitted from the drawing.

The body space 106 contains, for example, a pair of umbilical ligaments 108 and 110, whose retraction would aid dissection of the pelvic lymph nodes. The retractor 10 is introduced into the body space 106 through a piston or other member 112 pushing the retractor 10 in the direction of arrow 117 through the cannula 100 and into the body cavity 106. Two pairs of blunt tipped forceps 114 and 116, located in the cannulae 102 and 104, respectively, may be used to facilitate removal of the retractor 10 from the cannula 100 and introduction of the retractor 10 into the body cavity 106.

Figure 6A:
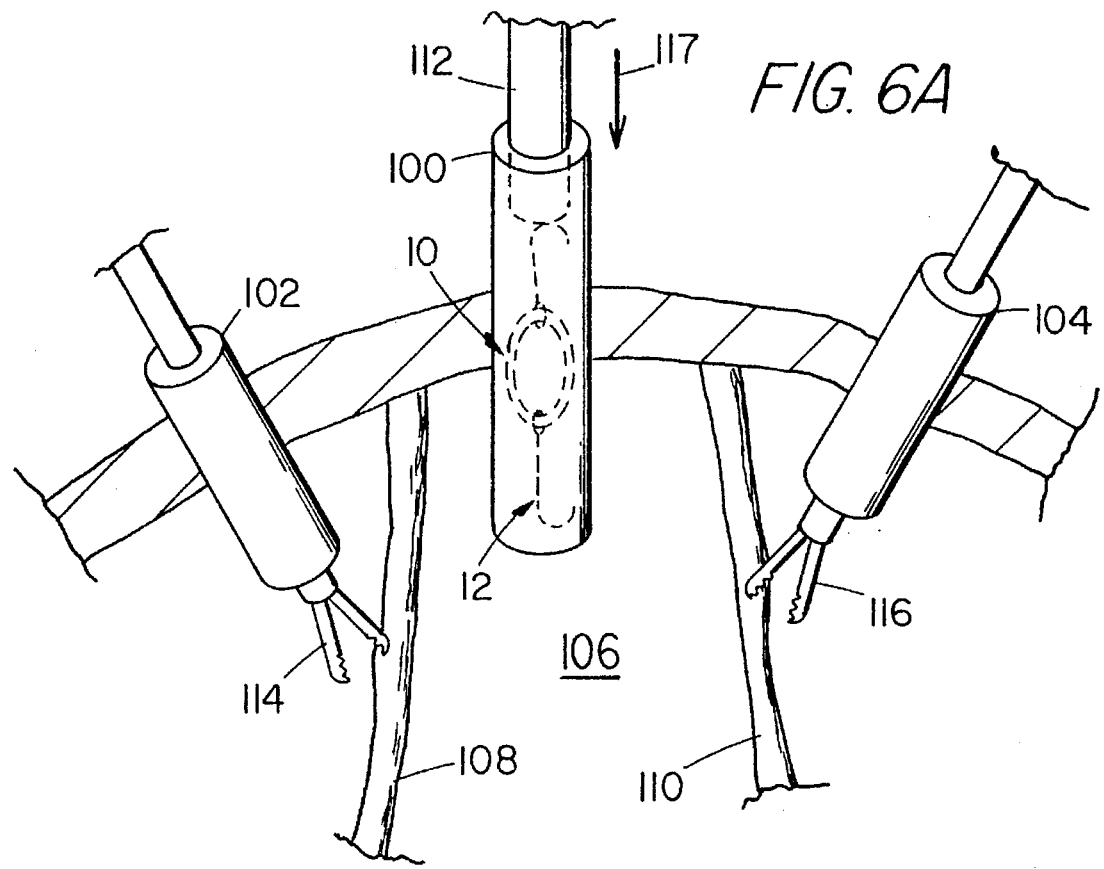
FIGS. 6A through 6C are simplified schematic views of a laparoscopic retraction performed with the preferred embodiment of the present invention.
Figure 6B:
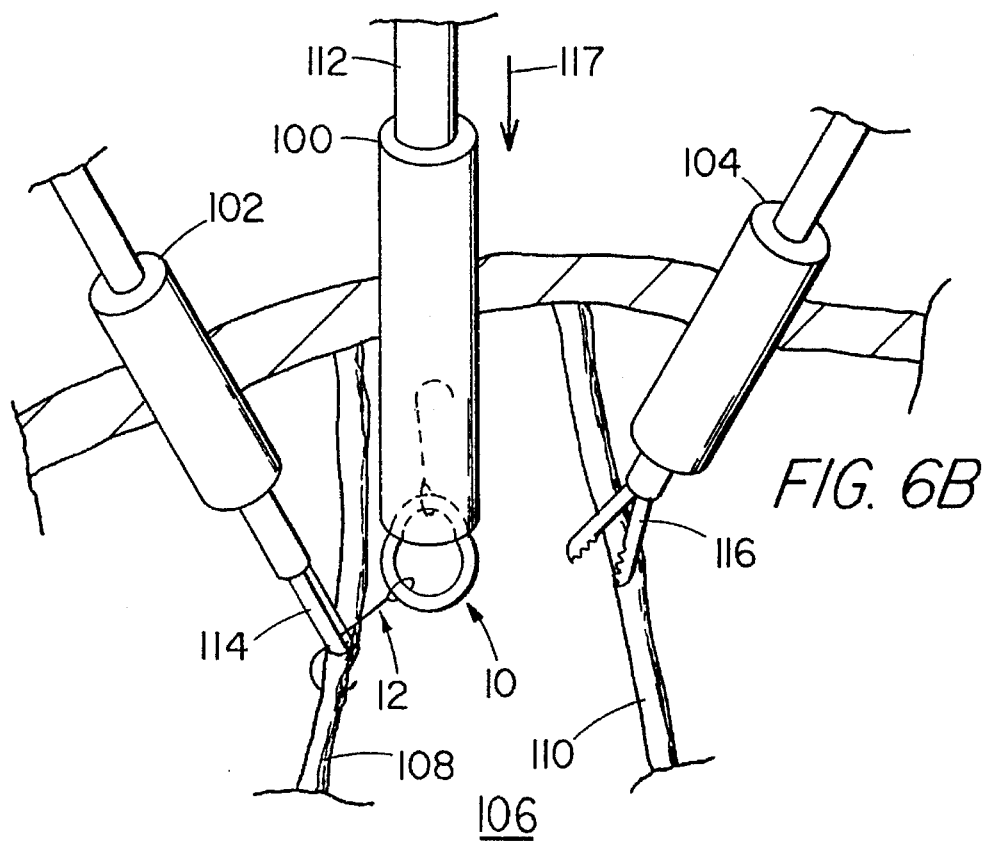
Figure 6C:
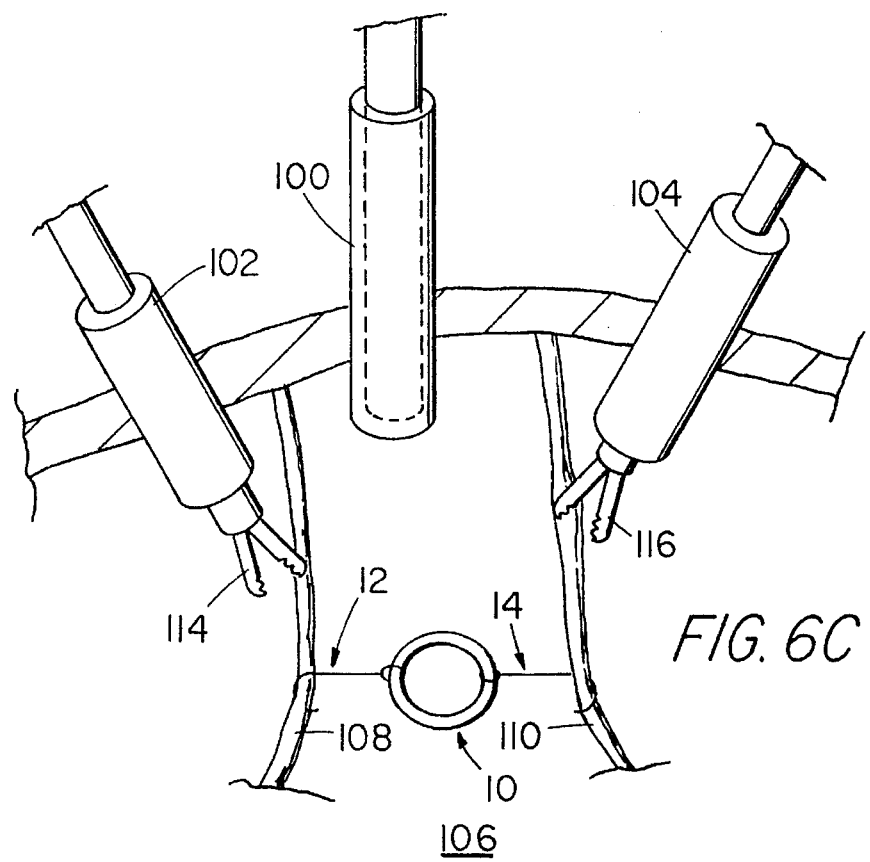

More particularly, as evident in FIG. 6A, the O-ring 22 or other elastic member 16 of the retractor 10 is collapsible in a direction transverse to an imaginary line drawn between the tissue-engaging elements 12 and 14, so as to allow the retractor to enter and pass through the cannula 100. The maximum interior diameter conventionally employed for laparoscopic cannulae is about 10 mm, and the elastic member 16 of the retractor 10 must therefore be collapsible to no more than that diameter. As shown in FIG. 6B, when the retractor 10 has been pushed far enough into the cannula 100 that one of the tissue-engaging elements (for example, the element 12) enters the body space 106, one of the pair of forceps (such as the forceps 114) can be manipulated by the surgeon to grasp the tissue-engaging element 12 and draw the retractor 10 out of the cannula 100 and fully into the body cavity 106. Alternatively, the piston or other pushing member 112 can be employed by itself to push the retractor 10 completely into the body cavity 106, and the forceps 114 and 116 employed to manipulate the retractor thereafter.

In either case, one of the forceps (such as the forceps 114) is then used to manipulate the tissue-engaging element 12 of the retractor 10 and cause it to engage the tissue to be retracted, for example, the umbilical ligament 108. The other forceps 116 is then used to manipulate the other tissue-engaging element 14 of the retractor 10 into engagement with the other (the contralateral) umbilical ligament 110, thereby achieving the retraction shown in FIG. 6C. Since the O-ring 22 or other member 16 of the retractor 10 is elastic, retraction of the umbilical ligaments 108 and 110 is successfully achieved without damage to them. Further, the relatively small profile of the retractor 10 permits the surgeon to maintain a very good view of the surgical site. Finally, the retractor 10 also provides excellent exposure of the obturator fossa when dissection of the pelvic lymph nodes is completed.

Removal of the retractor 10 from the body space 106 when the surgical procedure is completed is also straightforward. The forceps 114 and 116 are used to grasp the tissue-engaging elements 12 and 14, respectively, and remove them from the umbilical ligaments 108 and 110. Such removal is made easier by the fact that the central member 16 is elastic. The retractor 10, now disengaged from the ligaments 108 and 110, can be withdrawn by either of the forceps 114 and 116 through their respective cannula 102 or 104. Again, because the O-ring 22 or other elastic member 16 is collapsible in a direction transverse to the tissue-engaging elements 12 and 14, it does not hinder the withdrawal of the retractor 10 through the cannula 102 or 104. Such withdrawal is simpler than the introduction of the retractor 10 into the body space 106, and for brevity the withdrawal step is omitted from FIG. 6.

Figure 7:
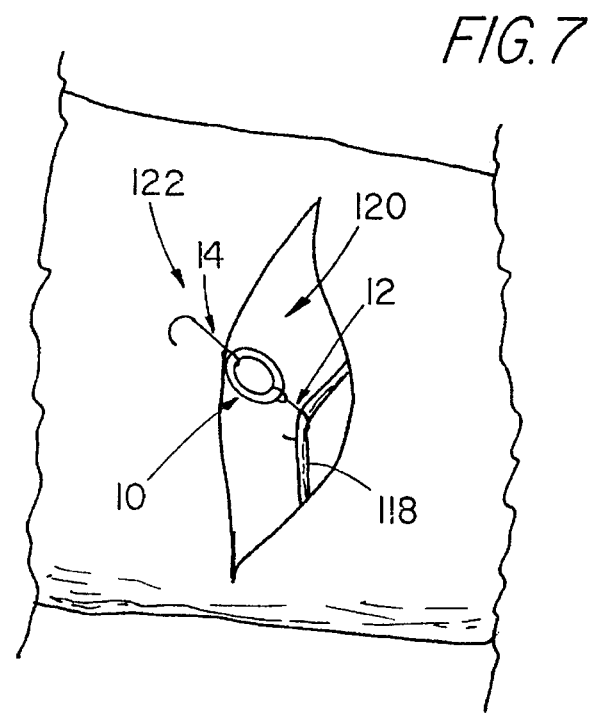
FIG. 7 is a simplified schematic view of a percutaneous retraction performed with the preferred embodiment of the present invention.

The retractor 10 of the present invention is also useful in open surgical procedures. Such use is shown schematically in FIG. 7, in which the retractor 10 has been used to retract an elongated body member 118 (such as a vessel, tendon or the like) exposed in an open surgical incision 120 made through the skin. The body member 118 is retracted by engagement with one of the tissue-engaging elements (for example, the element 12) of the retractor 10. Retraction is achieved by engaging the other tissue-engaging element 14 of the retractor 10 with another body portion; this portion is shown as the patient's skin 122 in FIG. 7, but can be any other suitable tissue of the patient.

The present invention thus provides a simple and inexpensive apparatus for the effective retraction of tissue during a variety of surgical procedures, particularly (but not exclusively) during laparoscopic or other endoscopic procedures. At the same time, the present invention may provide the first laparoscopic retractor or the like which is adapted to be wholly contained within the body space during laparoscopic surgery, significantly facilitating performance of that surgery.

Industrial Applicability

The present invention is useful in the performance of surgical procedures, and therefore finds applicability in human and veterinary medicine.

It is to be understood, however, that the above-described retractor or the like is merely an illustrative embodiment of the principles of this invention, and that other retractors or the like and methods for using them may be devised by those skilled in the art, without departing from the spirit and scope of the invention. It is also to be understood that the invention is directed to embodiments both comprising and consisting of the disclosed parts.

What is claimed is:

1. A surgical retractor, retainer, tensioner, tenaculum, spreader or stabilizer (10) particularly adapted for facile introduction into and removal from the body through a laparoscopic surgical cannula (100) during a laparoscopic procedure, comprising:

a plurality of tissue-engaging elements (12 and 14); and an elastic member (16) connecting the plurality of tissue-engaging elements (12 and 14);

wherein the elastic member (16) is collapsible into and through the laparoscopic surgical cannula (100), and wherein the plurality of tissue-engaging elements (12 and 14) are shaped and dimensioned so as to allow the retractor (10) to be passed through the laparoscopic surgical cannula (100) into and out of the body, so that the retractor (10) can be contained completely within the body during the laparoscopic procedure.

2. The surgical retractor (10) of claim 1, wherein the elastic member (16) comprises an O-ring (22).

3. The surgical retractor (10) of claim 1, wherein at least one (12 or 14) of the plurality of tissue-engaging elements (12 and 14) is slidable along the elastic member (16).

4. The surgical retractor (10) of claim 1, wherein the elastic member (16) is composed of a medical grade rubber, silicone or fluoropolymer elastomer.

5. The surgical retractor (10) of claim 1, wherein the elastic member (16) is shaped as a regular polygon (66, 74, 88, or 92).

6. The surgical retractor (10) of claim 1, wherein the plurality of tissue-engaging elements (12 and 14) are generally rigid.

7. The surgical retractor (10) of claim 1, wherein at least one (12 or 14) of the plurality of tissue-engaging elements (12 and 14) comprises an atraumatic hook (18).

8. The surgical retractor (10) of claim 1, wherein at least one (12 or 14) of the plurality of tissue-engaging elements (12 and 14) comprises a blade-type tissue-holding element (27).

9. The surgical retractor (10) of claim 1, wherein the elastic member (16) includes an interior brace (57) located between the plurality of tissue-engaging elements (12 and 14).

10. The surgical retractor (10) of claim 9, wherein the interior brace (57) is continuous with the remainder of the elastic member (16).

11. The surgical retractor (10) of claim 1, wherein the elastic member (16) includes an interior limiting web (80) located between the plurality of tissue-engaging elements (12 and 14).

12. A surgical retractor, retainer, tensioner, tenaculum, spreader or stabilizer (10) particularly adapted for facile introduction into and removal from the body through a laparoscopic surgical cannula (100) during a laparoscopic procedure, comprising:

a pair of tissue-engaging elements (12 and 14); and an elastic member (16) directly connecting the pair of tissue-engaging elements (12 and 14);

wherein the tissue-engaging elements (12 and 14) comprise atraumatic hooks (18);

wherein the elastic member (16) comprises an O-ring (22) composed of a medical grade silicone elastomer collapsible into and through the laparoscopic surgical cannula (100); and wherein the atraumatic hooks (18) are slidable along the O-ring (22) and are shaped and dimensioned so as to allow the retractor (10) to be passed through the cannula (100) into and out of the body;

so that the retractor (10) can be contained completely within the body, during the laparoscopic procedure.

13. A surgical retractor, retainer, tensioner, tenaculum, spreader or stabilizer (10) particularly adapted for facile introduction into and removal from the body through a laparoscopic surgical cannula (100) during a laparoscopic procedure, consisting essentially of:

a pair of tissue-engaging elements (12 and 14); and an elastic member (16) directly connecting the plurality of tissue-engaging elements (12 and 14);

wherein at least one of the tissue-engaging elements (12 and 14) consists of an atraumatic hook (18);

wherein the elastic member (16) is composed of a medical grade silicone elastomer;

wherein the tissue-engaging elements (12 and 14) include shank ends (24) looped about but not compressing the elastomer of the elastic member (16), whereby the tissue-engaging elements (12 and 14) are slidable along the elastic member (16); and wherein the elastic member (16) is collapsible into and through the laparoscopic surgical cannula (100), and wherein the pair of tissue-engaging elements (12 and 14) are shaped and dimensioned so as to allow the retractor (10) to be passed through the cannula (100) into and out of the body so that the retractor (10) can be contained completely within the body during the laparoscopic procedure.

14. The surgical retractor (10) of claim 13, wherein the elastic member (16) consists of an O-ring (22).

15. The surgical retractor (10) of claim 13, wherein the elastic member (16) is composed of a medical grade rubber, silicone or fluoropolymer elastomer.

16. The surgical retractor (10) of claim 13, wherein the elastic member (16) is shaped as a regular polygon (66, 74, 88, or 92).

17. The surgical retractor (10) of claim 13, wherein the pair of tissue-engaging elements (12 and 14) are generally rigid.

18. The surgical retractor (10) of claim 13, wherein each of tissue-engaging elements (12 and 14) consists of an atraumatic hook (18).

19. The surgical retractor (10) of claim 13, wherein the other of the pair of tissue-engaging elements (14 and 12) consists of blade-type tissue-holding element (27).

20. The surgical retractor (10) of claim 13, wherein the elastic member (16) includes an interior brace (57) located between the pair of tissue-engaging elements (12 and 14).

21. The surgical retractor (10) of claim 20, wherein the interior brace (57) is continuous with the remainder of the elastic member (16).

22. The surgical retractor (10) of claim 13, wherein the elastic member (16) includes an interior limiting web (80) located between the pair of tissue-engaging elements (12 and 14).

* * * * *